[19] United States Patent
Schmidt et al.

[11] Patent Number: 4,937,328
[45] Date of Patent: Jun. 26, 1990

[54] PROCESS FOR THE PREPARATION OF SPHINGOSINE DERIVATIVES

[75] Inventors: Richard R. Schmidt, Konstanz; Peter Zimmermann, Villingen, both of Fed. Rep. of Germany

[73] Assignee: Solco Basel AG, Basel, Switzerland

[21] Appl. No.: 895,181

[22] Filed: Aug. 11, 1986

[30] Foreign Application Priority Data

Aug. 13, 1985 [CH] Switzerland ............................ 3472/85
Mar. 7, 1986 [CH] Switzerland ............................. 938/86

[51] Int. Cl.$^5$ ............................................... C07H 5/06
[52] U.S. Cl. ................................. 536/18.6; 536/17.9; 536/18.5
[58] Field of Search ................ 536/17.9, 124, 18.5, 536/18.6

[56] References Cited

U.S. PATENT DOCUMENTS 4,415,733 11/1983 Tayot ................................. 536/55.1

OTHER PUBLICATIONS

Schmidt et al., Angew Chem. 94, 215–216 (1982).
Angew. Chem. Int. Ed. Engl. 21, 210–211 (1982).
Angew. Chem. Suppl. 1982, 393–397.
Reist et al., J. Org. Chem. 35, 3521–3524 (1970).
Newman, J. Am. Chem. Soc. 95, 4098–4099 (1973).
Tkaczuk et al., J. Org. Chem. 46, 4393–4398 (1981).
Bernet et al., Tetrahedron Letters 24, 5491–5494 (1983).
Koike et al., Glycoconjugate J. 1, 107–109 (1984).

Primary Examiner—Johnnie R. Brown
Assistant Examiner—Elli Peselev
Attorney, Agent, or Firm—Wenderoth, Lind & Ponack

[57] ABSTRACT

The invention relates to a new process for the preparation of the sphingosine derivatives described in European Patent Application No. 146,810, of the formula:

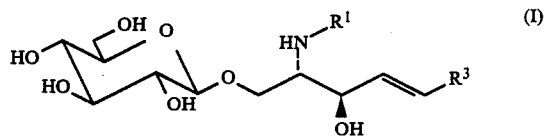

It comprises protecting D-galactose in the 4,6-position and oxidizing it to the corresponding D-threose protected in the 2,4-position, condensing an aliphatic chain ($R^3$) onto the latter by a Wittig reaction, converting the free hydroxyl group into a azido group and splitting off the protective group, protecting the resulting 2-azido-1,3-dihydroxy compound selectively in the 1-position and blocking it in the 3-position, liberating the 1-hydroxy group again, glycosidating the resulting compound or the abovementioned 2-azido-1,3-dihydroxy compound with the 0-trifluoro- or 0-trichloro-acetimade or the 1-halogen derivative of a 2,3,4,6-0-tetraacyl-D-glucose, splitting off the acyl groups of these and the protective group in the 3-position, converting the azido group into an amino group and acylating the amino compound with a fatty acid $R^1$—OH. The process gives the compounds of the therapeutically more active D series in a high yield in relatively few stages without resolving diastereomers.

19 Claims, 1 Drawing Sheet

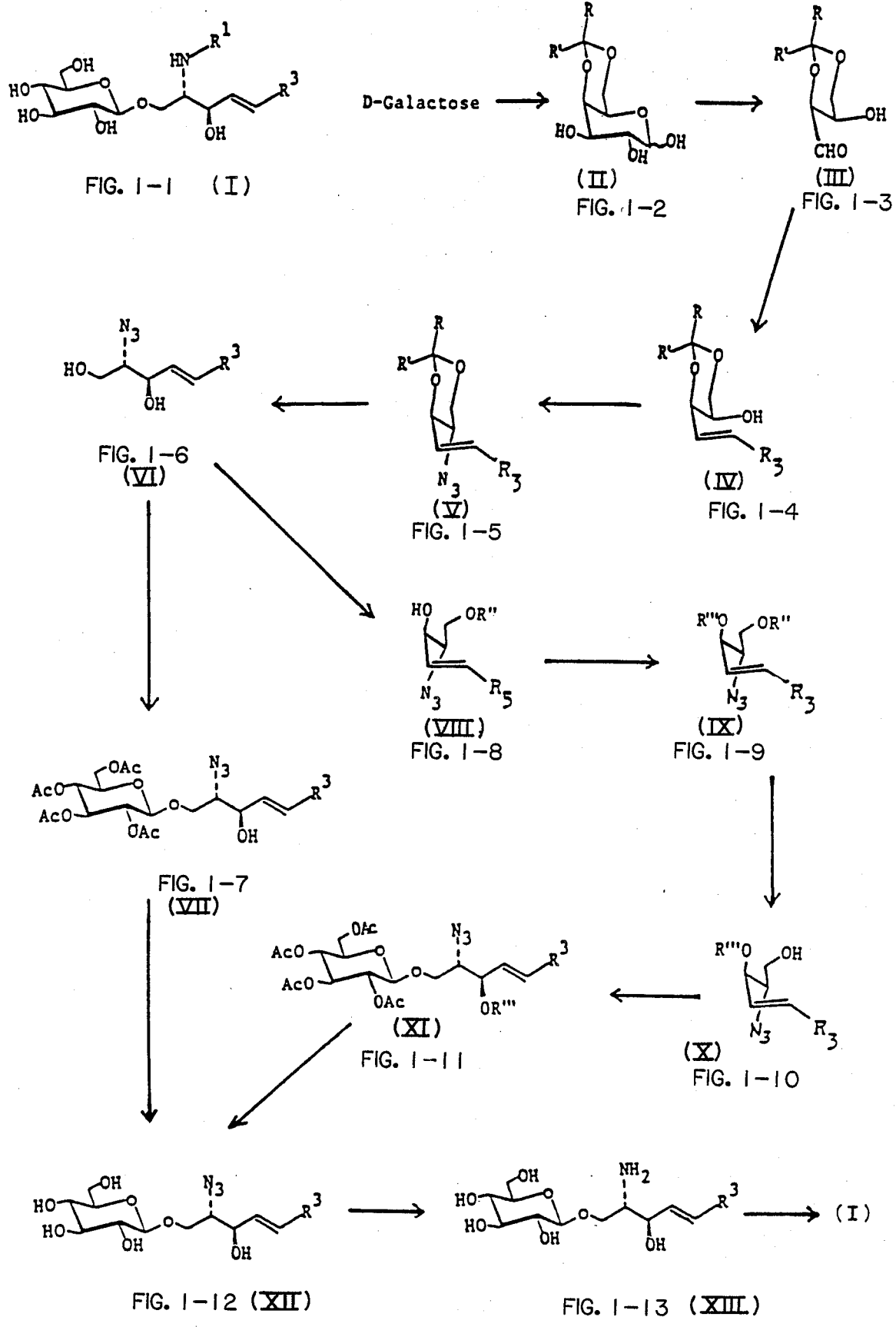

PROCESS FOR THE PREPARATION OF SPHINGOSINE DERIVATIVES

European Patent Application No. 84114415.7 (publication No. 146,810) relates to new sphingosine derivatives of the formulae:

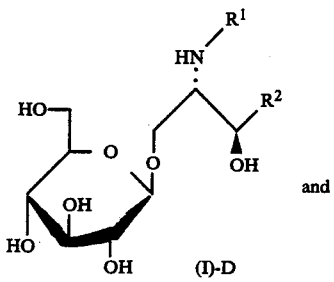

and

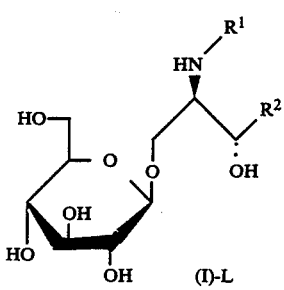

and processes for their preparation.

In the above formulae, $R^1$ denotes the acyl radical of a fatty acid with 14 to 24 carbon atoms or the corresponding acyl radicals with a hydroxyl group in the α-position or with one or two double bonds in the cis-configuration, and $R^2$ denotes the pentadecanyl or heptadecanyl radical or the corresponding $C_{15}$- and $C_{17}$-radicals with one, two or three double bonds, in each case one of which is in the 1,2-position and has the trans-configuration and the other or others, if present, have the cis-configuration.

These compounds have the erythro-configuration and correspond to the already known neutral glycosphingolipids. They are distinguished by wound healing-promoting or cell and tissue-regenerating properties and are suitable for therapeutic use on wounds of any origin, in particular wounds or ulcerations which heal poorly or slowly. They in fact lead, especially when applied topically to wounds, to the formation of healthy new tissue with good circulation, without troublesome scars. The sphingosine derivatives of the formula (I)-D are preferred, because of their higher therapeutic efficacy.

The preparation of the abovementioned compounds starts from corresponding ceramides of the formulae:

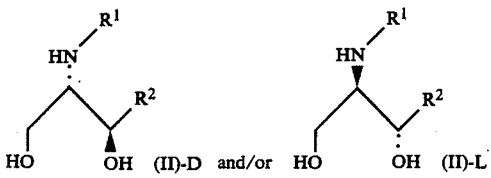

The ceramides in turn can be prepared from the $C_{18}$- or $C_{20}$-sphingosines by N-acylation by means of a fatty acid of the formula $R^1$-OH Depending on whether an optically active or a racemic sphingosine is used as the starting substance, the compounds of the formula (I)-D or (I)-L are obtained in an optically uniform form, or a mixture of the diastereomers (I)-D and (I)-L is obtained; in the latter case, the diastereomers must be resolved at a certain process stage.

It has recently been possible to obtain the racemic sphingosines in a good yield from glycine by a simple synthesis by R. R. Schmidt and R. Kläger [Angew. Chem. 94, 215–216 (1982); Angew. Chem. Int. Ed. Engl. 21, 210–211 (1982); and Angew. Chem. Suppl. 1982, 393–397]. Although the preparation process described above likewise gives a satisfactory yield of the sphingosine derivatives of the formula (I)-D or (I)-L, a process which manages without resolution of diastereomers would be preferable—especially considering that the more active compounds belong to the D series.

On the other hand, various syntheses are known which use a chiral compound selected ad hoc as the starting substance and thus lead, without resolution of diastereomers, to the optically active sphingosines of erythro-configuration and the D series, and therefore to the naturally occurring sphingosines.

The somewhat older synthesis of E. J. Reist and P. H. Christie [J. Org. Chem. 35, 3521 and 4127 (1970)], starting from D-glucose, and that of H. Newman [J. Am. Chem. Soc. 95, 4098 (1973)] and of P. Tkaczuk and E. R. Thornton [J. Org. Chem. 46, 4393 (1981)], both starting from L-serine, each comprise a reaction stage with a low yield, that is to say the preparation of 3-amino-3-deoxydi-(O-isopropylidene)-α-D-allofuranose or the addition reaction between trans-vinylalane and an aldehyde derived from L-serine.

A more recent synthesis of B. Bernet and A. Vasella [Tetrahedron Letters 24, 5491–5494 (1983)] gives D-erythro-$C_{18}$-sphingosine with an overall yield of 33% after 6 reaction stages. However, it starts from pentadecyne, which is not directly obtainable and the preparation of which has a detrimental effect on the number of stages and the overall yield.

Finally, the synthesis of a ceramide by K. Koike, Y. Nakahara and T. Ogawa [Glycoconjugate J. 1, 107–109 (1984)] which starts from a D-glucose derivative, comprises 12 reaction stages and gives the ceramide in a yield of about 20% should be mentioned. The process can probably be used for the preparation of sphingosines of naturally occurring configuration.

The use of optically active D-sphingosines as starting substances, which is in itself more advantageous, in the above preparation of sphingosine derivatives of the formula (I)-D has thus hitherto been impaired by the fact that provision of these starting substances is labour-intensive and/or unsatisfactory in yield.

It has now been found that optically uniform sphingosine derivatives of the formula (I)—see sheet of formulae—can be obtained by a new process which starts from commercially available D-galactose, comprises a total of 9 or 12 stages and gives the desired compounds in a satisfactory overall yield.

In formula (I), $R^1$ denotes the same acyl radicals as described above in the discussion of the formulae (I)-D and (I)-L, whilst $R^3$ represents an aliphatic radical with 13 to 19 carbon atoms, at least 13 of which are present in a straight chain and, if appropriate, not more than 4 are present as lateral methyl groups, it being possible for this radical to contain up to three double bonds of cis- or trans-configuration or up to three triple bonds.

The process according to the invention comprises reacting D-galactose with a lower aliphatic ketone or an aromatic aldehyde of the formula R—CO—R', in which R and R' each denote a lower alkyl radical or one of the radicals R and R' denotes a hydrogen atom and the other denotes an aromatic radical, to give a D-galactose protected in the 4- and 6-positions, of the formula (II), splitting this compound with an oxidizing agent which splits vicinal diols to give the corresponding D-threose protected in the 2- and 4-positions, of the formula (III), reacting the protected D-threose with an $R^3$-$CH_2$-phosphonate or an $R^3$-$CH_2$-triphenylphosphonium halide, in which $R^3$ has the above meaning, in the presence of a base or of a salt to give a compound of the formula (IV), converting the free hydroxyl group in this compound into an azido group by activation, liberating the resulting azido compound of the formula (V) from the protective group on the hydroxyl groups in the 1- and 3-positions of the aliphatic chain to form a 2-azido-1,3-dihydroxy compound of the formula (VI), reacting the latter with an organic reagent which is capable of reacting selectively with a primary hydroxyl group, to form a compound of the formula (VIII), in which R" denotes a hydroxyl-protective group, blocking the secondary hydroxyl group in the compound of the formula (VIII) with a protective group R''', splitting off the hydroxyl-protective group R" from the resulting compound of the formula (IX) to form a compound of the formula (X), glycosidating the compound previously obtained, of the formula (VI), or the compound of the formula (X) with the O-trifluoro- or O-trichloroacetimidate or the 1-halogen derivative of a D-glucose, the hydroxyl groups of which in the 2-, 3-, 4- and 6-positions are protected by acyl radicals Ac, to give a compound of the formula (VII) or (XI), splitting off the acyl groups Ac or the acyl groups Ac and the protective group R''' from the resulting compound to form the same compound of the formula (XII), converting the azido group in this into a primary amino group and subjecting the resulting compound of the formula (XIII) to N-acylation with a fatty acid of the formula $R^1$-OH.

The invention is described in more detail below.

The organic carboxylic acid $R^1$-OH from which the acyl group $R^1$ in the sphingosine derivatives of the formula (I) is derived is, for example, myristic acid $C_{14}H_{28}O_2$, palmitic acid $C_{16}H_{32}O_2$, stearic acid $C_{18}H_{36}O_2$, oleic acid $C_{18}H_{34}O_2$, linoleic acid $C_{18}H_{32}O_2$, arachidic acid $C_{20}H_{40}O_2$, behenic acid $C_{22}H_{44}O_2$ or—at the upper limit of the meaning given for $R^1$—tetracosanoic acid (lignoceric acid) $C_{24}H_{48}O_2$, cis-15-tetracosenoic acid (nervonic acid) $C_{24}H_{46}O_2$, 2-hydroxytetracosanoic acid (cerebronic acid) $C_{24}H_{48}O_3$, 2-hydroxy-15-tetracosenoic acid (hydroxynervonic acid) $C_{24}H_{46}O_3$ or the 2-hydroxy-17-tetracosenoic acid, which is isomeric with the previous acid.

The aliphatic radical $R^3$ can be an unbranched chain or can carry one, two, three or four methyl groups as substituents. The chain can furthermore be saturated or unsaturated; in the latter case, it contains one to three double bonds or one to three triple bonds. The double bonds have the cis- or the trans-configuration. Preferred aliphatic radicals $R^3$ are those with an uneven number of carbon atoms, in particular the $C_{13}$- and $C_{15}$-radicals.

In the first stage of the process, a lower aliphatic ketone, such as acetone, ethyl methyl ketone or diethyl ketone, or an aldehyde of the aromatic series, such as benzaldehyde or a benzaldehyde substituted on the phenyl ring, can be used to protect the hydroxyl groups in the 4- and 6-position of the D-galactose. The use of benzaldehyde is preferred for this. Suitable condensing agents for the reaction are in general Lewis acids, such as zinc chloride, boron trifluoride, aluminium chloride and iron chloride, or Brønsted acids, such as p-toluenesulphonic acid. The D-galactose can be converted into 4,6-O-benzylidene-D-galactose, for example, by the method of E. G. Gros and V. Deulofeu [J. Org. Chem. 29, 3647–3654 (1964)], and the reaction of D-galactose with acetone to give 4,6-O-isopropylidene-D-galactose can be carried out by the method of J. Gelas and D. Horton [Carbohydr. Res. 71, 103–121 (1979)].

The oxidizing agent used in the second process stage can be an alkali metal periodate, for example the lithium, sodium or potassium salt, or lead tetraacetate; sodium periodate is preferably used. The oxidation is advantageously carried out at a pH of about 7 to 8, for example in a corresponding buffer solution, at room temperature.

The Wittig reaction in the third stage of the process is as a rule carried out in an inert gas atmosphere, for example under nitrogen, at low temperatures, for example at $-10°$ to $-20°$ C., using an $R^3$-$CH_2$-phosphonium halide in the presence of a salt, for example lithium bromide, sodium chloride or potassium bromide. Suitable bases are, inter alia, organic lithium compounds, in particular phenyllithium, lithium methylate or lithium ethylate and furthermore sodium amide, sodium methylate and sodium carbonate. Solvents which can be used are aromatic hydrocarbons, such as benzene, toluene or xylene, or ethers, such as diethyl ether, tetrahydrofuran or dioxane; the solvent should be anhydrous.

The conversion of the free hydroxyl group into an azido group by activation can advantageously be carried out by O-sulphonation of the compound (IV) and subsequent reaction of the O-sulphonyl derivative formed, for example the methanesulphonyl, trifluoromethanesulphonyl or p-toluenesulphonyl derivative, with an alkali metal azide; inversion of the configuration on $C_2$ of the D-threose thereby takes place. The O-sulphonation can be carried out by the methods described in "Ullmanns Encyklopädie der technischen Chemie" ("Ullmann's Enoyclopaedia of Industrial Chemistry"), 4th edition, Volume 11, pages 91 et seq., Verlag Chemie GmbH, Weinheim FRG (1976). An acid halide or an acid anhydride of a lower aliphatic sulphonic acid or of a monocyclic aromatic sulphonic acid, for example methanesulphonyl chloride, p-toluenesulphonyl chloride, methanesulphonic acid anhydride or trifluoromethanesulphonic acid anhydride, is as a rule used. The O-sulphonation is preferably carried out in the presence of a base. Since anhydrous reaction conditions should be maintained and an organic solvent, such as benzene, toluene, tetrahydrofuran, diethyl ethyl or methylene chloride, is to be used, suitable bases are, in particular, tertiary organic bases, such as triethylamine, dimethylaniline, pyridine, collidine, lutidine and the like. The subsequent reaction with the alkali metal azide, for example lithium azide, sodium azide or potassium azide, is advantageously carried out without purification of the O-sulphonyl derivative. Both reactions are preferably carried out in an inert gas atmosphere, of example under nitrogen, at low temperatures or room temperature.

In the fifth stage of the process, the protective group can be split off from the compound (V) by acid hydrolysis. For example, the compound is dissolved in an organic solvent, such as methylene chloride or dimethylformamide, and a small amount of concentrated hydrochloric acid and water is then allowed to act on the solution for some time, preferably at room temperature.

The compound (VI) can now be subjected directly to glycosidation to form a compound (VII), or can be converted, via the intermediate products (VIII), (IX) and (X), into a compound (XI), which only then is subjected to glycosidation. Although this second process variant comprises three more reaction stages, it gives a higher overall yield and is therefore particularly suitable for production on an industrial scale. It is explained in more detail below.

Protection of the primary hydroxyl group of the 2-azido-1,3-dihydroxy compound (VI) should be carried out with reagents which, in the presence of a primary and a secondary hydroxyl group, react selectively with the former. Particularly suitable protective groups R″ are thus those which occupy a large space, such as, for example, the tert.-butyl, triphenylmethyl (trityl), trichloroacetyl, trimethylsilyl, tert.-butyldimethylsilyl or tert.-butyldiphenylsilyl group. The triphenylmethyl, monomethoxytriphenylmethyl, tert.-butyldimethylsilyl and tert.-butyldiphenylsilyl group are preferred.

The protective group R″ is introduced by the known methods of organic chemistry, depending on the nature of the protective group chosen. For example, the triphenylmethyl group can be introduced by treatment of the compound (VI) with a corresponding halide, such as triphenylchloromethane or triphenylbromomethane. The corresponding halide, preferably the chloride or the bromide, can also advantageously be used for the tert.-butyldimethylsilyl and the tert.-butyldiphenylsilyl group.

The compound protected in the 1-position, of the formula (VIII), is then protected on the hydroxyl group in the 3-position by a protective group R‴, for example by a tert.-butoxycarbonyl group, by esterification with an organic carboxylic acid Ac′OH or a reactive functional derivative thereof. Simple, aliphatic carboxylic acids and aromatic, in particular monocyclic aromatic, carboxylic acids, above all, are suitable for this; the use of benzoic acid, a substituted benzoic acid or pivalic acid is preferred.

The esterification with the carboxylic acid Ac′OH can be carried out by the methods described in "Ullmanns Enoyklopädie der technischen Chemie" ("Ullmann's Encyclopaedia of Industrial Chemistry"), 4th edition, Volume 11, pages 91 et seq., Verlag Chemie GmbH, Weinheim FRG (1976). It is advantageously carried out using a carboxylic acid halide in the presence of a tertiary organic base, such as triethylamine, pyridine or dimethylaniline, in an anhydrous organic solvent, such as benzene, toluene, tetrahydrofuran, diethyl ether or methylene chloride.

The protective group R″ on the hydroxyl group in the 1-position of the compound of the formula (IX) can be split off by acid hydrolysis (triphenylmethyl protective groups and silyl protective groups) or by treatment with boron trifluoride-etherate (triphenylmethyl groups). The compound of the formula (X), in which the hydroxyl group in the 3-position is still blocked by the protective group R‴ but the primary hydroxyl group in the 1-position is free again, is obtained.

The reaction of the compound (IX) or that of the compound (VI) with the O-trichloro- or O-trifluoroacetimidate of a D-glucose, the hydroxyl groups of which, apart from that on the 1-position, are protected by acyl radicals Ac, is advantageously catalysed by a Lewis acid, such as boron trifluoride-etherate or trimethylsilyltrifluoromethanesulphonate. It is in general carried out in an anhydrous organic solvent, such as a hydrocarbon (hexane) or a halogenated hydrocarbon (methylene chloride). Acyl radicals which are used to protect the hydroxyl groups in the 2-, 3-, 4- and 6-positions of the D-glucose are, preferably, lower aliphatic acyl groups, such as the acetyl, propionyl, pivaloyl, trifluoroacetyl or methanesulphonyl group. Details on the preparation of the reagent can be found in the publication by R. R. Schmidt and M. Stumpp (Liebigs Ann. Chem. 1983, 1249–1256) and R. R. Schmidt, J. Michel and M. Roos (Liebigs Ann. Chem. 1984, 1343–1357).

The corresponding reaction with the 1-halogen derivative of the O-tetraacylated D-glucose, for example with O-acetyl-α-D-glucopyranosyl chloride or bromide (the latter is also called α-D-O-acetobromoglucose), is as a rule carried out in the presence of a heavy metal compound, such as silver oxide, a heavy metal salt, such as silver carbonate or mercury cyanide, or an organic base, which function as an acid-binding agent (Ullmanns Enoyklopädie der technischen Chemie (Ullmann's Encyclopaedia of Industrial Chemistry), 4th edition, Volume 24, page 757, Verlag Chemie GmbH, Weinheim FRG 1983).

Splitting off of the acyl radicals Ac and the protective group R‴ from the compound (VII) or (XI) is in general catalysed by bases; the use of sodium methanolate in anhydrous methanol at room temperature is particularly advantageous for this.

In the penultimate stage of the process, the conversion of the azido group into the primary amino group is best effected by treatment of the compound (XII) with hydrogen sulphide at room temperature. For this, the compound is dissolved, for example, in a mixture (1:1) of water and pyridine. The same conversion can also be carried out by hydrogenation with sodium borohydride or another reducing agent, such as, for example, sodium cyanoborohydride.

The N-acylation of the compound (XIII) with the organic carboxylic acid of the formula $R^1$-OH (last stage of the process) can be carried out by the method of D. Shapiro and co-workers [J. Am. Chem. Soc. 86, 4472 (1964)]. In general, the carboxylic acid itself, in the presence of a dehydrating agent, such as dicyclohexylcarbodiimide in methylene chloride, or a functional reactive derivative of the carboxylic acid, such as an activated ester or a halide, in the presence of an inorganic base, such as sodium acetate, or of a tertiary organic base, is used. The N-acylation is advantageously carried out at room temperature.

The compounds obtained at each process stage are isolated and purified by the customary methods of organic chemistry.

The following examples illustrate preferred embodiments of the invention.

$^1$H-NMR spectra were recorded with the 250 MHz apparatus WM 250 Cryospec from Bruker, Spectrospin, Industriestrasse 26, CH-8117 Fällanden/Zürich. The shifts are based on tetramethylsilane (TMS) as the internal standard and are stated in ppm.

The melting points stated were determined on a copper block and are uncorrected.

Silica gel plates from E. Merck AG, Darmstadt (FRG) were used for the analytical thin layer chromatography (TLC). Where the substances were not UVactive, the thin layer chromatograms were sprayed with 15% strength sulphuric acid and developed at 120° C.

Preparative column chromatography was carried out with silica gel 60 (0.062–0.200 mm) from Merck. Prepacked columns according to D. Flockerzi, Degree thesis, Stuttgart University/FRG (1978) containing the silica gel "LiChroprep Si 60, 15–25" were used for the medium pressure chromatography.

The yields have been stated at the purification stage at which no impurities were to be detected by NMR spectroscopy and by means of thin layer chromatography.

The figures in parentheses against the solvent mixtures denote parts by volume.

EXAMPLE 1

2S,3R-2-Hexadecanoylamino-3-hydroxy-1-($\beta$-D-glucopyranosyloxy)-4-trans-eicosene (a) 4,6-O-Benzylidene-D-galactose See J. Org. Chem. 29, 3647–3654 (1964).

(b) 2,4-O-Benzylidene-D-threose (1)

30 g (0.111 mol) of 4,6-O-benzylidene-D-galactose are dissolved in about 1,200 ml of phosphate buffer of pH 7.6. 55 g (0.257 mol) of sodium periodate are added, while stirring vigorously. The pH is kept at about 7 to 8 by dropwise addition of 2N sodium hydroxide solution. The mixture is stirred at room temperature for 1.5 hours. Thereafter, it is concentrated to dryness under a water-pump vacuum. The solid residue is extracted four times with 250 ml of ethyl acetate each time. The extract is filtered, dried over magnesium sulphate and concentrated.

Yield: 20 g (85%), $R_F=0.64$ in toluene/ethanol (3:1).

(c) 2R,3R-1,3-O-Benzylidene-2-hydroxy-4-trans-eicosene (2)

70 g (0.12 mol) of hexadecyltriphenylphosphonium bromide are suspended under nitrogen in about 1 liter of anhydrous toluene saturated with nitrogen. Phenyllithium which has been prepared from 6.5 g (0.94 mol) of lithium and 74 g (0.47 mol) of bromobenzene in about 200 ml of anhydrous ether is added dropwise without further purification. At the same time, the mixture is cooled to −15° C. Thereafter, 20 g (0.096 mol) of compound (I) in about 150 ml of anhydrous tetrahydrofuran are added dropwise in the course of 20 minutes, under nitrogen. After a further 20 minutes, first 150 ml of methanol and then 250 ml of water are added. The mixture is stirred vigorously. After removal of the aqueous phase, the organic phase is concentrated. For purification, the residue is chromatographed over silica gel with petroleum ether/ethyl acetate (9:1).

Yield: 27 g (68%), $R_F=0.21$ in petroleum ether/etnyl acetate (9:1).

(d) 2S,3R-2-Azido-1,3-O-benzylidene-4-trans-eicosene (3)

10 g (0.025 mol) of compound (2) are dissolved in about 70 ml of anhydrous methylene chloride containing 5 ml of anhydrous pyridine. The solution is cooled to −15° C., under nitrogen. 8.12 g (0.029 mol) of trifluoromethanesulphonic acid anhydride are slowly added dropwise. After 15 minutes, the mixture is filtered over silica gel and eluted with methylene chloride/petroleum ether (1:1). The receiver is flushed continuously with nitrogen. The eluate is concentrated and the oil which remains is taken up in 50 ml of anhydrous dimethylformamide. 7.5 g (0.1 mol) of sodium azide are added, under nitrogen. The mixture is stirred at room temperature for 2 hours. Thereafter, it is diluted with about 350 ml of methylene chloride and filtered and the filtrate is concentrated under a waterpump vacuum. For purification, the residue is chromatographed over silica gel with petroleum ether/ethyl acetate (9:1).

Yield: 8 g (75%), $R_F=0.8$ in petroleum ether/ethyl acetate (9:1).

(e) 2S,3R-2-Azido-1,3-dihydroxy-4-trans-eicosene (4)

8 g (0.018 mol) of compound (3) are dissolved in 100 ml of methylene chloride. 5 ml of concentrated chloric acid and 3 ml of water are added and the mixture is stirred vigorously at room temperature for 12 hours. Thereafter, it is extracted by shaking with aqueous sodium bicarbonate solution. The organic phase is separated off, dried over sodium sulphate and concentrated. For purification, the residue is chromatographed over silica gel with methylene chloride/methanol (95:5).

Yield: 4.32 g (68%), $R_F=0.46$ in methylene chloride/methanol (95:5), melting point: 56°–57° C.

Elemental analysis: calculated C 67.95, H 11.11, N 11.88, found 67.62, 11.12, 11.85.

$^1$H-NMR (250 MHz, CDCl$_3$ in ppm) of compound (4): 5.83 (m, 1H, —CH$_2$—C$\underline{H}$=C); 5.55 (dd, 1H, —CH$_2$—CH=C$\underline{H}$—, J=15.5 Hz, J=6.5 Hz); 4.25 (m, 1H, —C$\underline{H}$—N$_3$); 3.8 (m, 2H, —CH$_2$—O$\underline{H}$, C$\underline{H}$—O$\underline{H}$); 3.52 (m, 1H, —C$\underline{H}_2$—OH); 2.05 (m, 4H, OH, C=CH—C$\underline{H}_2$); 1.45–1.18 (m, 26H, aliphatic); and 0.88 (t, 3H, C$\underline{H}_3$).

(f) 2S,3R-2-Azido-3-hydroxy-1-(2,3,4,6-tetra-O-acetyl-$\beta$-D-glucopyranosyloxy)-4-trans-eicosene (6)

0.5 g (1.41 mmol) of compound (4) is dissolved in 50 ml of anhydrous hexane. 0.1 ml of 0.5M boron trifluoride-etherate in methylene chloride and a spatula-tip of molecular sieve 4 Å are added. 0.7 g (1.41 mmol) of O-(2,3,4,6-tetra-O-acetyl-$\alpha$-D-glucopyranosyl)-tricnloroacetimidate is dissolved in 3 ml of anhydrous toluene and the solution is slowly added dropwise. After 4 hours, the mixture is washed with 30 ml of saturated sodium bicarbonate solution. The aqueous phase is extracted three times by shaking with 30 ml of methylene chloride each time. The organic phases are dried over sodium sulphate and concentrated. For purification, the residue is chromatographed over silica gel with methylene chloride/methanol (97.5:2.5).

Yield: 0.385 g (40%), $R_F=0.7$ in methylene chloride/methanol (95:5).

$^1$H-NMR (250 MHz, CDCl$_3$ in ppm) of compound (6): 5.78 (m, 1H, —CH$_2$—C$\underline{H}$=C); 5.5 (dd, 1H, —CH$_2$—CH=C$\underline{H}$—, J=15.5 Hz, J=7.3 Hz); 5.3–4.98 (m, 3H, H-2, $\underline{H}$-3, H-4); 4.58 (d, 1H, H-1, J=7.6 Hz); 4.35–4.13 (m, 3H, H-6, H-6; —C$\underline{H}$—N$_3$); 4.05 (dd, 1H, —C$\underline{H}_2$—O—); 3.73 (m, 2H, H-5, —C$\underline{H}_2$—O); 3.47

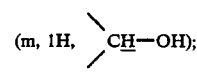

(m, 1H, $\diagdown$C$\underline{H}$—OH);

2.24 (d, 1H, OH, J=4.8 Hz); 2.16–1.94 (m, 14H, acetyl, C=CH—C$\underline{H}_2$); 1.45–1.15 (m, 26H, aliphatic); and 0.88 (t, 3H, —C$\underline{H}_3$).

(g)
2S,3R-2-Azido-3-hydroxy-1-(β-D-glucopyranosyloxy)-4-trans-eicosene (7)

0.4 g (0.585 mol) of compound (6) is dissolved in 30 ml of anhydrous methanol. 0.2 ml of a 1M solution of sodium methylate in methanol is added. The mixture is stirred at room temperature for one hour. Thereafter, it is neutralized with the ion exchanger Amberlit IR 120 (H⊕ form). The ion exchanger is filtered off, the filtrate is concentrated and the residue is chromatographed over silica gel with chloroform/methanol (9:1).

Yield: 0.26 g (86%), $R_F$=0.22 in chloroform/methanol (9:1).

$^1$H-NMR (250 MHz, DMSO-$d_6$ in ppm) of compound (7): 4.10 (d, 1H, H-1, J=7.6 Hz).

(h)
2S,3R-2-Amino-3-hydroxy-1-(β-D-glucopyranosyloxy)-4-trans-eicosene (8)

0.26 g (0.5 mmol) of compound (7) is dissolved in a mixture of 4 ml of pyridine and 4 ml of water. The solution is saturated with hydrogen sulphide. The mixture is stirred at room temperature for 24 hours. It is concentrated to dryness and the residue is chromatographed over silica gel, first with chloroform/methanol (6:4) and then with chloroform/methanol/water (5:4:1).

Yield: 0.234 g (96%), $R_F$=0.65 in chloroform/methanol/water (5:4:1).

$^1$H-NMR (250 MHz, DMSO-$d_6$ in ppm) of compound (8): 4.10 (d, 1H, H-1, J=7.6 Hz).

(i)
2S,3R-2-Hexadecanoylamino-3-hydroxy-1-(β-D-glucopyranosyloxy)-4-trans-eicosene (9)

0.23 g (0.47 mmol) of compound (8) is dissolved in 5 ml of tetrahydrofuran. 5 ml of a 50% strength aqueous sodium acetate solution are added. 0.19 g (0.7 mmol) of hexadecanoyl chloride is added to the mixture at room temperature, with vigorous stirring. After about 2 hours, the organic phase is separated off. The aqueous phase is extracted three times by shaking with 2 ml of chloroform each time. The organic phases are dried over sodium sulphate and concentrated. For purification, the residue is chromatographed over silica gel with chloroform/methanol (9:1).

Yield: 0.3 g (90%), $R_F$=0.50 in chloroform/methanol (9:1).

$^1$H-NMR (250 MHz, DMSO-$d_6$ in ppm) of compound (9): 7.5 (d, 1H, NH, J=8.7 Hz); 5.52 (m, 1H, —CH$_2$—CH=C); 5.35 (dd, 1H, C=CH—, J=15.2 Hz, J=6.5 Hz); 5.03 (d, 1H, OH, J=3.4 Hz); 4.92 (m, 3H, OH); 4.5 (t, 1H, OH, J=4.9 Hz); 4.09 (d, 1H, H-1, J=7.6 Hz); 4.0-3.55 (m, 4H); 3.45 (m, 2H); 3.15-2.9 (m, 4H); 2.1-1.88 (m, 4H); 1.45 (m, 2H); 1.22 (m, 54H, aliphatic); and 0.85 (m, 6H, CH$_3$).

Appendix

To confirm the structure attributed to the compound of the formula (VI), compound (4) was subjected to the same treatment with hydrogen sulphide (see below), as is described in section (h) of the preceding example. Compound (5) was in fact thereby obtained, its physicochemical properties coinciding completely with those of erythro-D-$C_{18}$-sphingosine prepared from natural sources.

2S,3R-2-Amino-1,3-dihydroxy-4-trans-eicosene (5)

0.25 g (0.7 mmol) of compound (4) is dissolved in a mixture of 5 ml of pyridine and 2 ml of water. The solution is saturated with hydrogen sulphide. The mixture is stirred at room temperature for 48 hours. It is concentrated to dryness. The residue is chromatographed over silica gel, first with chloroform, then with chloroform/methanol (9:1) and finally with chloroform/methanol/water (8:2:0.25).

Yield: 0.215 g (95%), $R_F$=0.2 in chloroform/methanol (1:1), melting point: 70°-72° C.

$^1$H-NMR (250 MHz, CDCl$_3$ in ppm) of compound (5): 5.78 (m, 1H, —CH$_2$—CH=C); 5.47 (dd, 1H, —CH$_2$—CH=CH—, J=15.5 Hz, J=7.3 Hz); 4.12 (dd, 1H, C=CH—CH—OH, J=6.1 Hz); 3.7 (m, 2H, CH$_2$—OH); 2.93 (m, 1H, —CH—NH$_2$); 2.57 (m, 4H, NH$_2$, OH); 2.06 (m, 2H, C=CH—CH$_2$); 1.45-1.18 (m, 26 H, aliphatic); and 0.88 (t, 3H, —CH$_3$).

EXAMPLE 2
2S,3R-2-Hexadecanoylamino-3-hydroxy-1-(β-D-glucooyranosyloxy)-4-trans-octadecene

(j)
2R,3R-1,3-O-Benzylidene-2-hydroxy-4-trans-octadecene (10)

70 g (0.13 mol) of tetradecyltriphenylphosphonium bromide are suspended under nitrogen in about 1 liter of anhydrous toluene saturated with nitrogen. Phenyllithium which has been prepared from 6.5 g (0.94 mol) of lithium and 74 g (0.47 mol) of bromobenzene in about 200 ml of anhydrous ether is added dropwise, without further purification. At the same time, the mixture is cooled to −15° C. Thereafter, 21.6 g (0.104 mol) of 2,4-O-benzylidene-D-threose [see Example 1, compound (1)] in about 150 ml of anhydrous tetrahydrofuran are added dropwise in the course of 20 minutes, under nitrogen. After a further 20 minutes, first 150 ml of methanol and then 250 ml of water are added. The mixture is stirred vigorously. After removal of the aqueous phase, the organic phase is concentrated. For purification, the residue is chromatographed over silica gel with petroleum ether/ethyl acetate (9:1).

Yield: 27 g (68%), $R_F$=0.21 in petroleum ether/ethyl acetate (9:1), melting point: 54°-55° C.

(k)
2S,3R-2-Azido-1,3-O-benzylidene-4-trans-octadecene (11)

10 g (0.025 mol) of compound (10) are dissolved in about 70 ml of anhydrous methylene chloride containing 5 ml of anhydrous pyridine. The solution is cooled to −15° C., under nitrogen. 8.7 g (0.31 mol) of trifluoromethanesulphonic acid anhydride are slowly added dropwise. After 15 minutes, the mixture is filtered over silica gel and eluted with methylene chloride/petroleum ether (1:1). The receiver is flushed continuously with nitrogen. The eluate is concentrated and the oil which remains is taken up in 50 ml of anhydrous dimethylformamide. 7.5 g (0.1 mol) of sodium azide are added, under nitrogen. The mixture is stirred at room temperature for 2 hours. Thereafter, it is diluted with about 350 ml of methylene chloride and filtered and the filtrate is concentrated under a waterpump vacuum. For purification, the residue is chromatographed over silica gel with petroleum ether/ethyl acetate (9:1).

Yield: 7.8 g (75%), $R_F$=0.8 in petroleum ether/ethyl acetate (9:1).

(l) 2S,3R-2-Azido-1,3-dihydroxy-4-trans-octadecene (12)

7 g (0.017 mol) of compound (11) are dissolved in 100 ml of methylene chloride. 5 ml of concentrated hydrochloric acid and 3 ml of water are added and the mixture is stirred vigorously at room temperature for 12 hours. Thereafter, it is extracted by shaking with aqueous sodium bicarbonate solution. The organic phase is separated off, dried over sodium sulphate and concentrated. For purification, the residue is chromatographed over silica gel with methylene chloride/methanol (95:5).

Yield: 3.76 g (68%), $R_F$=0.46 in methylene chloride/methanol (95:5).

$^1$H-NMR (250 MHz, CDCl$_3$ in ppm) of compound (12): 5.83 (m, 1H, CH$_2$—CH=C); 5.55 (dd, 1H, —CH$_2$—CH=CH—, J=15.5 Hz, J=6.5 Hz); 4.25 (m, 1H, —CH—N$_3$); 3.8 (m, 2H, —CH$_2$—OH,

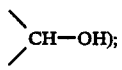

3.52 (m, 1H, —CH$_2$—OH); 2.05 (m, 4H, OH, C=CH—CH$_2$); 1.45–1.18 (m, 22H, aliphatic); and 0.88 (t, 3H, CH$_3$).

(m) 2S,3R-2-Azido-3-hydroxy-1-O-triphenylmethyl-4-trans-octadecene (13)

4 g (12.3 mmol) of compound (12) are dissolved in 45 ml of a mixture of in each case anhydrous pyridine/chloroform/tetrahydrofuran (1:1:1). 6 g (21.5 mmol) of trityl chloride are added. The mixture is stirred at room temperature for 48 hours. Thereafter, it is concentrated under a waterpump vacuum. The residue is taken up in 200 ml of diethyl ether and the mixture is extracted by shaking with 100 ml of water. The organic phase is dried over magnesium sulphate and concentrated. For purification, the residue is chromatographed over silica gel with petroleum ether/ethyl acetate (9:1).

Yield: 6.3 g (90%), $R_F$=0.39 in petroleum ether/ethyl acetate (9:1).

$^1$H-NMR (250 MHz, CDCl$_3$ in ppm) of compound (13): 7.55–7.15 (m, 15H, aromatic); 5.75–5.58 (m, 1H, CH$_2$—CH=C); 5.38–5.26 (dd, 1H, CH$_2$—CH=CH—, J=15.5 Hz, J=7.3 Hz); 4.20 (m, 1H, —CH—N$_3$); 3.53 (m, 1H, —CH—OH); 3.30 (d, 2H, O—CH$_2$—, J=5.4 Hz); 2.03–1.188 (m, 3H, —OH, CH=CH—CH$_2$); 1.40–1.10 (m, 22H, aliphatic); and 0.88 (t, 3H, CH$_3$).

(n) 2S,3R-2-Azido-3-benzoyloxy-1-O-triphenylmethyl-4-trans-octadecene (14)

6.3 g (11.1 mmol) of compound (13) are dissolved in 30 ml of a mixture of in each case anhydrous toluene/pyridine (4:1). 3 g (21.3 mmol) of benzoyl chloride are added. The mixture is stirred at room temperature for 12 hours. Thereafter, it is poured onto about 200 ml to water and extracted twice with 100 ml of diethyl ether each time. The organic phase is dried over magnesium sulphate and concentrated. For purification, the residue is chromatographed over silica gel with petroleum ether/ethyl acetate (95:5).

Yield: 6.7 g (90%), $R_F$=0.60 in petroleum ether/ethyl acetate (9:1).

(o) 2S,3R-2-Azido-3-benzoyloxy-1-hydroxy-4-trans-octadecene (15)

6.7 g (9.97 mmol) of compound (14) are dissolved in a mixture of 30 ml of anhydrous toluene and 5 ml of anhydrous methanol. 10 ml of 3M boron trifluoride-etherate in methylene chloride are added. After 5 hours, the mixture is poured onto 50 ml of water and the organic phase is separated off. After drying over magnesium sulphate, the organic phase is concentrated and the residue is chromatographed first with petroleum ether/ethyl acetate (9:1) and then with petroleum ether/ethyl acetate (8:2).

Yield: 3.8 g (90%), $R_F$=0.13 in petroleum ether/ethyl acetate (9:1).

Elemental analysis for C$_{25}$H$_{39}$N$_{39}$N$_3$O$_3$ (molecular weight 429.56) calculated: C 69.90, H 9.14, N 9.78, found: 69.92, 9.16, 9.65.

$^1$H-NMR (250 MHz, CDCl$_3$ in ppm) of compound (15): 8.14 (m, 2H, aromatic); 7.58 (m, 1H, aromatic); 7.47 (m, 2H, aromatic); 6.05–5.87 (m, 1H, CH$_2$—CH=C); 5.69–5.53 (m, 2H, CH$_2$—CH=CH—, CH—OBz); 2.15–1.95 (m, 3H, —OH, C=CH$_2$H); 1.47–1.13 (m, 22H, aliphatic); and 0.86 (t, 3H, CH$_3$).

(p) 2S,3R-2-Azido-3-benzoyloxy-1-(2,3,4,6-tetra-O-pivaloyl-β-D-glucopyranosyloxy)-4-trans-octadecene (16)

2 g (4.6 mmol) of compound (15) and 4.6 g (7.0 mmol) of 2,3,4,6-tetra-O-pivaloyl-α-D-glucopyranosyltrichloroacetimidate are dissolved in 40 ml of anhydrous methylene chloride and the solution is stirred with molecular sieve 4 Å for 30 minutes. Thereafter, 0.2 ml of 0.1M boron trifluoride-etherate in methylene chloride is added. A further 2 ml of 0.1M boron trifluoride-etherate are added in portions of in each case 0.5 ml in the course of the reaction. After 48 hours, the mixture is diluted with 200 ml of petroleum ether and filtered. The filtrate is extracted by shaking with 50 ml of aqueous sodium bicarbonate solution and the organic phase is dried over sodium sulphate and concentrated. For purification, the residue is chromatographed over silica gel with toluene/acetone (97.5:2.5).

Yield 4 g (94%), $R_F$=0.57 in toluene/acetone (97.5:2.5).

$^1$H-NMR (250 MHz, CDCl$_3$ in ppm) of compound (16): 8.05 (m, 2H, aromatic); 7.58 (m, 1H, aromatic); 7.45 (m, 2H, aromatic); 5.99–5.83 (m, 1H, CH$_2$—CH=C); 5.65–5.46 (m, 2H, CH$_2$—CH=CH, CH—OBz); 5.37–5.02 (m, 3H, H-2, H-3, H-4); 4.58 (d, 1H, H-1, 1=7.9 Hz); 4.25–3.58 (m, 6H, H-6, H-6', H-5, CH—N$_3$, CH$_2$—O); 2.06 (m, 2H, CH=CH—CH$_2$); 1.45–1.04 (m, 58H, pivaloyl, aliphatic); and 0.89 (t, 3H, CH$_3$).

(q) 2S,3R-2-Azido-3-hydroxy-1-(β-D-glucopyranosyloxy)-4-trans-octadecene (17)

4 g (4.3 mmol) of compound (16) are dissolved in 50 ml of anhydrous methylene chloride. 8 ml of a 0.05M sodium methylate solution in anhydrous methanol are added. The mixture is stirred at room temperature for three days. Thereafter, it is neutralized with the ion exchanger Amberlit JR 120 (H⊕ form). The ion exchanger is filtered off, the filtrate is concentrated and the residue is chromatographed over silica gel with chloroform/methanol (8.5:1.5).

Yield: 1.65 g (78%), $R_F=0.20$ in chloroform/methanol (9:1).

$^1$H-NMR (250 MHz, DMSO-$d_6$ in ppm) of compound (17): 4.10 (d, 1H, H-1, J=7.6 Hz).

(r)
2S,3R-2-Amino-3-hydroxy-1-($\beta$-D-glucopyranosyloxy)-4- trans-octadecene (18)

1.65 g (3.4 mmol) of compound (17) are dissolved in 50 ml of a mixture of pyridine/water (1:1). The solution is saturated with hydrogen sulphide. The mixture is stirred at room temperature for 24 hours. It is concentrated to dryness and chromatographed over silica gel, first with chloroform/methanol (9:1) and then with chloroform/methanol/water (5:4:1).

Yield: 1.47 g (94%) $R_F=0.64$ in chloroform/methanol/water (5:4:1).

$^1$H-NMR (250 MHz, DMSO-$d_6$ in ppm) of compound (18): 4.10 (d, 1H, H-1, J=7.6 Hz).

(s)
2S,3R-2-Hexadecanoylamino-3-hydroxy-1-($\beta$-D-glucopyranosyloxy)-4-trans-octadecene (19)

1.47 g (3.2 mmol) of compound (18) are dissolved in 50 ml of tetrahydrofuran. 50 ml Of a 50% aqueous sodium acetate solution are added. 0.87 g (3.2 mmol) of hexadecanoyl chloride are added to the mixture at room temperature, with vigorous stirring. After about 2 hours, the mixture is diluted with 350 ml of tetrahydrofuran and the aqueous phase is removed. The organic phase is extracted by shaking twice with 50 ml of saturated sodium chloride solution each time and is concentrated. The residue is dried under a high vacuum. For purification, the residue is chromatographed over silica gel, first with chloroform and then with chloroform/methanol (9:1)

Yield: 1.81 g (81%), $R_F=0.4$ in chloroform/methanol (8.5:1.5).

$^1$H-NMR (250 MHz, DMSO-$d_6$ in ppm) of compound (19): 7.5 (d, 1H, NH, J=8.7 Hz); 5.52 (m, 1H, —CH$_2$—CH═C); 5.35 (dd, 1H, CH$_2$—CH═CH—, J=15.2 Hz, $\overline{J}$=6.5 Hz); 5.03 (d, 1H, OH, J=3.4 $\overline{Hz}$); 4.92 (m, 3H, OH); 4.5 (t, 1H, OH, J=4.9 Hz); 4.09 (d, 1H, H-1, J=7.6 Hz); 4.0–3.55 (m, 4H); 3.45 (m, 2H); 3.15–2.9 (m, 4H); 2.1–1.88 (m, 4H); 1.45 (m, 2H); 1.22 (m, 50H aliphatic); and 0.85 (t, 6H, CH$_3$.)

We claim:

1. A process for preparation of sphingosine derivatives of the formula (I)

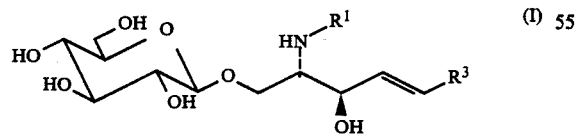

(I)

in which $R^1$ denotes an acyl radical of a fatty acid with 14 to 24 carbon atoms or the corresponding acyl radical with a hydroxyl group in the α-position or with one or two double bonds in the cis-configuration, and $R^3$ denotes an aliphatic radical with 13 to 19 carbon atoms, at least 13 carbon atoms of which are present in a straight chain and 0–4 carbon atoms of which are present as lateral methyl groups, said aliphatic radical containing 0–3 double bonds of cis- or trans-configuration or 0–3 triple bonds, which process comprises:

reacting D-galactose with a lower aliphatic ketone or an aromatic aldehyde of the formula R—CO-R' in which R and R' each denote a lower alkyl radical or one of the radicals R and R' denotes a hydrogen atom and the other denotes an aromatic radical, to give a D-galactose protected in the 4- and 6-positions, of the formula (II)

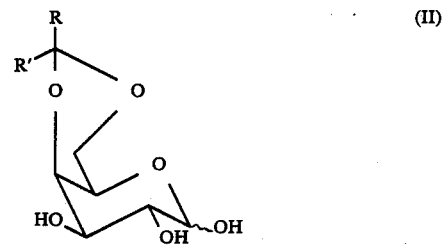

(II)

in which R and R' have the above meanings, reacting the protected D-galactose with an alkali metal periodate or lead tetraacetate, to give the corresponding D-threose protected in the 2- and 4-positions, of the formula (III)

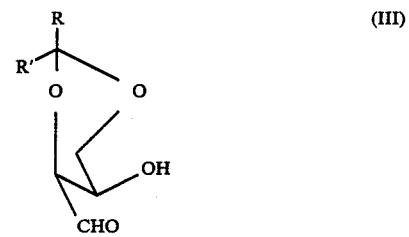

(III)

in which R and R' have the above meanings, reacting the protected D-threose with an $R^3$—CH$_2$-phosphonate or an $R^3$—CH$_2$-triphenylphosphonium halide, in which $R^3$ has the above meaning, in the presence of a base or of a base and a salt to give a compound of the formula (IV)

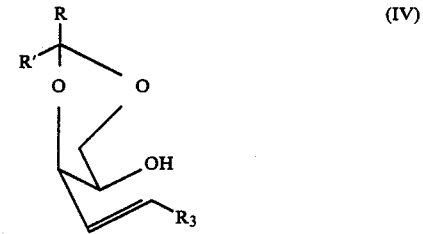

(IV)

in which R, R' and $R^3$ have the above meanings, sulphonating the free hydroxyl group in the compound of formula (IV) with an acid halide or an acid anhydride of a lower aliphatic sulphonic acid or of a monocyclic aromatic sulphonic acid and reacting the resultant O-sulphonyl derivative with an alkali metal azide, to give an azido compound of the formula (V)

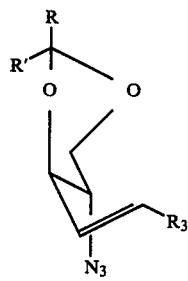

(V)

in which R, R' and R³ have the above meanings,
removing the protective groups on the hydroxyl groups in the 1- and 3-positions of the aliphatic chain in the compound of formula (V) by acid hydrolysis to form a 2-azido-1, 3-dihydroxy compound of the formula (VI)

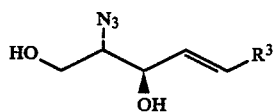

(VI)

in which R³ has the above meaning,
glycosidating the compound of formula VI with the O-trifluoro- or O-trichloro-acetimidate or the 1-halogen derivative of a D-glucose, the hydroxyl groups of which in the 2-, 3-, 4- and 6-positions are protected by acyl radicals Ac, to give a compound of the formula (VII)

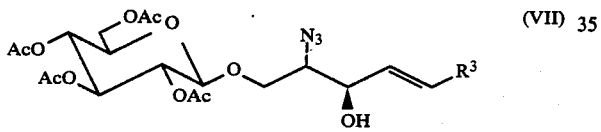

(VII)

in which Ac and R³ have the above meanings, and removing the acyl groups Ac from the compound of formula (VII) by basic catalysis to form a compound of the formula (XII)

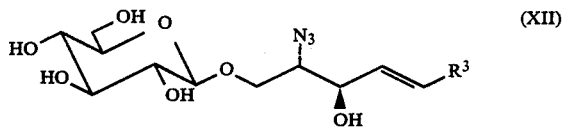

(XII)

in which R³ has the above meaning,
treating the compound of formula (XII) with hydrogen sulphide, sodium borohydride or sodium cyanoborohydride to convert the azido group in the compound of formula (XII) into a primary amino group, to give a compound of the formula (XIII)

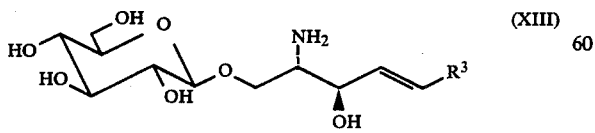

(XIII)

in which R³ has the above meaning, and
subjecting the compound of formula (XIII) to N-acylation with a fatty acid of the formula R¹-OH in which R¹ is as defined above, or with a functional reactive derivative of the fatty acid, to form the compound of formula (I).

2. The process according to claim 1, wherein the reaction of the protected D-galactose with the alkali metal periodate or lead tetraacetate is carried out at a pH of about 7 to 8 at room temperature.

3. A process for preparation of sphingosine derivatives of the formula (I)

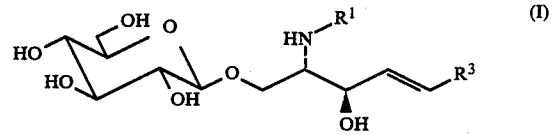

(I)

in which $R^1$ denotes an acyl radical of a fatty acid with 14 to 24 carbon atoms or the corresponding acyl radical with a hydroxyl group in the α-position or with one or two double bonds in the cis-configuration, and $R^3$ denotes an aliphatic radical with 13 to 19 carbon atoms, at least 13 carbon atoms of which are present in a straight chain and 0–4 carbon atoms of which are present as lateral methyl groups, said aliphatic radical containing 0–3 double bonds of cis- or trans-configuration or 0–3 triple bonds, which process comprises:

reacting D-galactose with a lower aliphatic ketone or an aromatic aldehyde of the formula R—CO-R, in which R and R' each denote a lower alkyl radical or one of the radicals R and R' denotes a hydrogen atom and the other denotes an aromatic radical, to give a D-galactose protected in the 4- and 6-positions, of the formula (II)

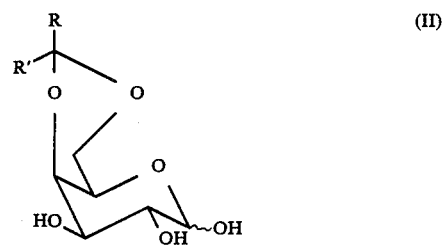

(II)

in which R and R' have the above meanings,
reacting the protected D-galactose with an alkali metal periodate or lead tetraacetate, to give the corresponding D-threose protected in the 2- and 4-positions, of the formula (III)

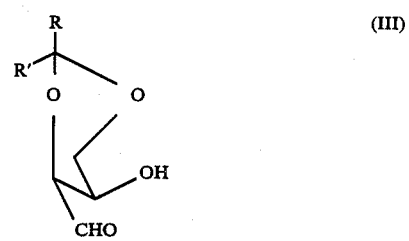

(III)

in which R and R' have the above meanings,
reacting the protected D-threose with an R³—CH₂-phosphonate or an R³—CH₂-triphenylphosphonium halide, in which R³ has the above meaning, in the presence of a base or of a base and a salt to give a compound of the formula (IV)

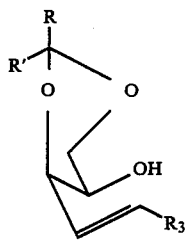

(IV)

in which R, R' and R³ have the above meanings, sulphonating the free hydroxyl group in the compound of formula (IV) with an acid halide or an acid anhydride of a lower aliphatic sulphonic acid or of a monocyclic aromatic sulphonic acid and reacting the resultant O-sulphonyl derivative with an alkali metal azide, to give an azido compound of the formula (V)

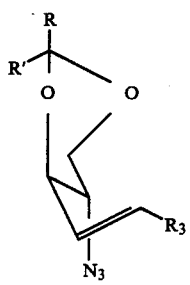

(V)

in which R, R' and R³ have the above meanings, removing the protective groups on the hydroxyl groups in the 1- and 3-positions of the aliphatic chain in the compound of formula (V) by acid hydrolysis to form a 2-azido-1,3-dihydroxy compound of the formula (VI)

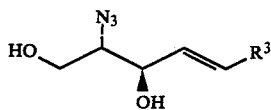

(VI)

in which R³ has the above meaning, reacting the compound of formula (VI) with an organic reagent which is capable of reacting selectively with a primary hydroxyl group, to form a compound of the formula (VIII)

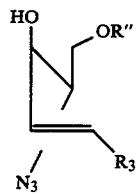

(VIII)

in which R″ denotes a hydroxyl-protective group and R³ has the above meaning, esterifying the secondary hydroxyl group in the compound of formula (VIII) with an organic carboxylic acid Ac'OH or a reactive functional derivative thereof, wherein Ac' is acyl to give a compound of the formula (IX)

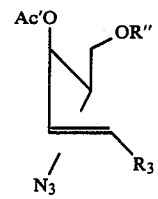

(IX)

in which R″, Ac' and R³ have the above meanings, removing the hydroxyl-protective group R″ from the compound of formula (IX) by acid hydrolysis or treatment with boron trifluoride-etherate to form a compound of the formula (X)

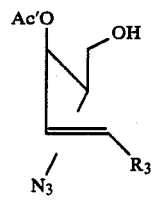

(X)

in which Ac' and R³ have the above meanings, glycosidating the compound of formula (X) with the O-trifluoro- or O-trichloro-acetimidate or the 1-halogen derivative of a D-glucose, the hydroxyl groups of which in the 2-, 3-, 4- and 6-positions are protected by acyl radicals Ac, to give a compound of the formula (XI)

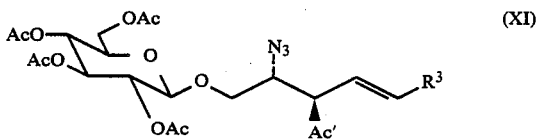

(XI)

in which Ac, R³ and Ac' have the above meanings, and removing the acyl groups Ac and Ac' from the compound of formula (XI) by basic catalysis to form a compound of the formula (XII)

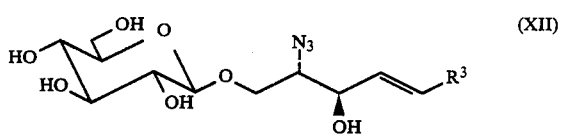

(XII)

in which R³ has the above meaning, treating the compound of formula (XII) with hydrogen sulphide, sodium borohydride or sodium cyanoborohydride to convert the azido group in the compound of formula (XII) into a primary amino group, to give a compound of the formula (XIII)

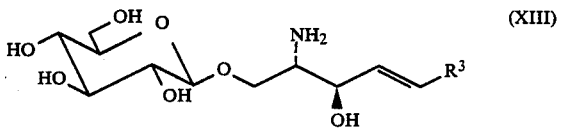

(XIII)

in which R³ has the above meaning, and subjecting the compound of the formula (XIII) to N-acylation with a fatty acid of the formula R¹—OH in which R¹ is as defined above, or with a functional reactive derivative of the fatty acid, to form the compound of formula (1).

4. The process according to claim 3, wherein acetone, ethyl methyl ketone or diethyl ketone, or benzaldehyde or a benzaldehyde substituted on the phenyl ring is used as the aldehyde or ketone of the formula R—CO—R'.

5. The process according to claim 3, wherein the reaction of the protected D-galactose with the alkali metal periodate or lead tetraacetate is carried out at a pH of about 7 or 8 at room temperature.

6. The process according to claim 3, wherein the glycosidation of the compound of the formula (X) as defined in claim 3 with the said O-trifluoro- or O-trichloro-acetimidate is carried out in the presence of a Lewis acid catalyst and in an anhydrous hydrocarbon or halogenated hydrocarbon, and that with the said 1-halogen derivative is carried out in the presence of an acid-binding agent or a heavy metal salt.

7. The process according to claim 3, wherein the azido group of the compound of the formula (XII) as defined in claim 3 is converted into a primary amino group by treatment with hydrogen sulphide in a 1:1 mixture of water and pyridine or by hydrogenation with sodium borohydride or sodium cyanoborohydride.

8. The process according to claim 3, wherein the N-acylation of the compound of the formula (XIII) as defined in claim 3 is carried out by means of the fatty acid of the formula $R^1$—OH as defined in claim 3 in the presence of a dehydrating agent or by means of an activated ester of the fatty acid or by means of a halide thereof in the presence of an inorganic base or a tertiary organic base.

9. The process according to claim 3, wherein the reaction of the protected D-threose of the formula (III) with the $R^3$—$CH_2$-phosphonate or the $R^3$—$CH_2$-triphenylphosphonium halide wherein $R^3$ is as defined in claim 3 is carried out in the presence of phenyllithium, lithium methylate, lithium ethylate, sodium amide, sodium methylate or sodium carbonate in an anhydrous hydrocarbon or ether under a nitrogen atmosphere at a temperature of $-10°$ to $-20°$ C. and, when using the $R^3$—$CH_2$-triphenylphosphonium halide, with the addition of a salt.

10. The process according to claim 3, wherein the sulphonation of the free hydroxyl group of the compound of the formula (IV) as defined in claim 3 is carried out by O-trifluoromethanesulphonation, methanesulphonation or p-toluenesulphonation.

11. The process according to claim 1, wherein acetone, ethyl methyl ketone or diethyl ketone, or benzaldehyde or a benzaldehyde substituted on the phenyl ring is, used as the aldehyde or ketone of the formula R—CO—R'.

12. The process according to claim 3, wherein a triphenylmethyl, monomethoxytriphenylmethyl, tert.-butyl, trichloroacetyl, trimethylsilyl, tert.-butyldimethylsilyl or tert.-butyldiphenylsilyl group is used as the hydroxyl-protective group R".

13. The process according to claim 1, wherein the glycosidation of the compound of the formula (VI) as defined in claim 19 with the said O-trifluoro- or O-trichloro-acetimidate is carried out in the presence of a Lewis acid catalyst and in an anhydrous hydrocarbon or halogenated hydrocarbon, and that with the said 1-halogen derivative is carried out in the presence of an acid-binding agent or a heavy metal salt.

14. The process according to claim 1, wherein the azido group of the compound of the formula (XII) as defined in claim 1 is converted into a primary amino group by treatment with hydrogen sulphide in a 1:1 mixture of water and pyridine or by hydrogenation with sodium borohydride or sodium cyanoborohydride.

15. The process according to claim 1, wherein the N-acylation of the compound of the formula (XIII) as defined in claim 1 is carried out by means of the fatty acid of the formula $R^1$—OH as defined in claim 1 in the presence of a dehydrating agent or by means of an activated ester of the fatty acid or by means of a halide thereof in the presence of an inorganic base or a tertiary organic base.

16. The process according to claim 1, wherein the reaction of the protected D-threose of the formula (III) as defined in claim 1 with the $R^3$—$CH_2$-phosphonate or the $R^3$—$CH_2$-triphenylphosphonium halide wherein $R^3$ is as defined in claim 1 is carried out in the presence of phenyllithium, lithium methylate, lithium ethylate, sodium amide, sodium methylate or sodium carbonate in an anhydrous hydrocarbon or ether under a nitrogen atmosphere at a temperature of $-10°$ to $-20°$ C. and, when using the $R^3$—$CH_2$-triphenylphosphonium halide, with the addition of a salt.

17. The process according to claim 1, wherein the sulphonation of the free hydroxyl group of the compound of the formula (IV) as defined in claim 1 is carried out by O-trifluoromethanesulphonation, methanesulphonation or p-toluenesulphonation.

18. The process according to claim 3, wherein an acyl radical of an aliphatic or aromatic carboxylic acid or a tert.-butoxycarbonyl group is used as the protective group Ac'.

19. The process according to claim 18, wherein the acyl radical is an acyl radical of benzoic acid, a substituted benzoic acid or pivalic acid.

* * * * *